(12) United States Patent
Ravishankar et al.

(10) Patent No.: US 9,237,760 B2
(45) Date of Patent: Jan. 19, 2016

(54) COATED PHARMACEUTICAL OR NUTRACEUTICAL PREPARATION WITH ENHANCED ACTIVE SUBSTANCE RELEASE IN THE COLON

(75) Inventors: Hema Ravishankar, Chembur (IN); Shraddha Bodinge, Mumbai (IN); Hans-Ulrich Petereit, Darmstadt (DE)

(73) Assignee: EVONIK RÖHM GmbH, Darmstadt (DE)

( * ) Notice: Subject to any disclaimer, the term of this patent is extended or adjusted under 35 U.S.C. 154(b) by 0 days.

(21) Appl. No.: 12/742,842

(22) PCT Filed: Feb. 1, 2008

(86) PCT No.: PCT/EP2008/051236
§ 371 (c)(1),
(2), (4) Date: May 13, 2010

(87) PCT Pub. No.: WO2009/086940
PCT Pub. Date: Jul. 16, 2009

(65) Prior Publication Data
US 2010/0247639 A1 Sep. 30, 2010

(30) Foreign Application Priority Data
Jan. 10, 2008 (IN) ............... 95/CHE/2008

(51) Int. Cl.
*A61K 9/00* (2006.01)
*A61K 9/28* (2006.01)
*A61K 9/48* (2006.01)
*A23L 1/00* (2006.01)
*A23L 1/22* (2006.01)
*A61K 9/50* (2006.01)

(52) U.S. Cl.
CPC ........... *A23L 1/0029* (2013.01); *A23L 1/22016* (2013.01); *A61K 9/5078* (2013.01)

(58) Field of Classification Search
CPC ... A61K 9/2866; A61K 9/2846; A61K 9/284; A61K 9/2833; A61K 47/32
See application file for complete search history.

(56) References Cited

U.S. PATENT DOCUMENTS

| | | | |
|---|---|---|---|
| 6,458,389 B1 | 10/2002 | Debregeas et al. | |
| 6,632,454 B2 * | 10/2003 | Beckert et al. | 424/482 |
| 6,878,387 B1 * | 4/2005 | Petereit et al. | 424/490 |
| 2002/0192282 A1 | 12/2002 | Beckert et al. | |
| 2004/0091534 A1 * | 5/2004 | Geoghegan et al. | 424/471 |
| 2004/0258749 A1 | 12/2004 | Guldner et al. | |
| 2005/0152977 A1 | 7/2005 | Petereit et al. | |
| 2005/0191352 A1 | 9/2005 | Hayes et al. | |
| 2006/0269605 A1 | 11/2006 | Lizio et al. | |
| 2007/0042045 A1 | 2/2007 | Lizio et al. | |
| 2008/0044470 A1 | 2/2008 | Petereit et al. | |
| 2008/0206324 A1 | 8/2008 | Gryczke et al. | |
| 2010/0129446 A1 | 5/2010 | Liu et al. | |

FOREIGN PATENT DOCUMENTS

| | | |
|---|---|---|
| CN | 1364077 A | 8/2002 |
| CN | 1446083 A | 10/2003 |
| DE | 198 45 358 A1 | 4/2000 |
| DE | 100 13 029 | 9/2001 |
| JP | 2002-526401 A | 8/2002 |
| JP | 2005-505589 A | 2/2005 |
| WO | WO 01/68058 A1 | 9/2001 |
| WO | WO 03/030869 A | 4/2003 |
| WO | WO 2004/039357 A1 | 5/2004 |
| WO | 2004 096185 | 11/2004 |
| WO | 2005 046561 | 5/2005 |
| WO | 2005 046649 | 5/2005 |
| WO | WO 2008/135090 A1 | 11/2008 |

OTHER PUBLICATIONS

Wu, Chuanbin; McGinity, J.W. Influence of an Enteric Polymer on Drug Release Rates of Theophylline from Pellets Coated with Eudragit RS 30D. Pharmaceutical Development and Technology, 2003, vol. 8, No. 1, 103-110.*
Raw Machine Translation provided by Espacenet for the claims and description of WO03030869 accessed on Aug. 21, 2013.*
http://eudragit.evonik.com/product/eudragit/en/products-services/eudragit-products/enteric-formulations/s-100/pages/default.aspx referenced on Aug. 21, 2013.*
http://eudragit.evonik.com/product/eudragit/en/products-services/eudragit-products/enteric-formulations/1-100-55/pages/default.aspx as referenced on Feb. 3, 2014.*
U.S. Appl. No. 60/908,854, filed Mar. 29, 2007, Gryczke, et al.
U.S. Appl. No. 12/742,263, filed May 11, 2010, Ravishankar, et al.
U.S. Appl. No. 12/742,945, filed May 14, 2010, Ravishankar, et al.
Israeli Office Action issued Feb. 6, 2012, in Patent Application No. 205488 (English translation only).

(Continued)

*Primary Examiner* — Robert A Wax
*Assistant Examiner* — Jessica Worsham
(74) *Attorney, Agent, or Firm* — Oblon, McClelland, Maier & Neustadt, L.L.P.

(57) ABSTRACT

The present invention relates to a pharmaceutical or nutraceutical preparation comprising a) a core containing a pharmaceutically or nutraceutically active substance; and b) an inner controlling layer surrounding the core comprising i) one or a mixture of a plurality of (meth)acrylate copolymers bearing a cationic group or a group that can be converted to a cationic group; and ii) one or a mixture of a plurality of polymers or copolymers bearing an anionic group or group that can be converted to an anionic group; and c) an outer controlling layer comprising one or a mixture of a plurality of polymers or copolymers bearing an anionic group or group that can be converted to an anionic group and to tablets or capsules comprising same.

22 Claims, No Drawings

(56) References Cited

OTHER PUBLICATIONS

Chinese Office Action (in English) issued Jun. 12, 2012 in connection with corresponding Chinese Application No. 200880118177.4, filed Feb. 1, 2008.

Office Action issued Jan. 4, 2013, in Japanese Patent Application No. 2010-541717 (submitting English translation only).

Office Action issued Apr. 14, 2014 in Canadian Patent Application No. 2,711,473.

Office Action issued May 28, 2014 in Israel Patent Application No. 205488 (submitting English translation only).

Office Action issued Jun. 27, 2014 in Indian Patent Application No. 4164/CHENP/2010.

* cited by examiner

COATED PHARMACEUTICAL OR NUTRACEUTICAL PREPARATION WITH ENHANCED ACTIVE SUBSTANCE RELEASE IN THE COLON

The invention relates to a new multi layer coated pharmaceutical or nutraceutical preparation, to medicament forms containing such preparations and to the use of certain copolymers comprising anionic groups or groups that can be converted to anionic groups in an inner controlling layer comprising certain polymers containing cationic groups or groups that can be converted to cationic groups that surround a core containing a pharmaceutically or nutraceutically active substance in order to increase the release rate of the pharmaceutically or nutraceutically active substance or enable a more complete drug release from controlled release dosage forms in the colon.

PRIOR ART

From the prior art many different approaches are known how to control the release of pharmaceutically active substances from pharmaceutical preparations. Different solutions are provided depending on where and in which time frame the pharmaceutically active substance shall be released in the digestive system when using oral application forms.

Several prior art documents are known that describe multilayer coated pharmaceutical preparations in order to adjust specific release patterns for the pharmaceutically active component.

WO 2005/046649, WO 2005/046561, WO 2006/102964 and WO 2006/102965 all relate to multiparticulate pharmaceutical preparations having a multilayer coating that permits to adjust the permeability of the film coatings by intrinsic modulations in order to achieve specific release profiles. This is achieved by a multiparticulate pharmaceutical form comprising a core, an inner controlling layer surrounding the core that comprises a substance having a modulating effect, especially salts of organic acids, which is embedded in a matrix of pharmaceutically acceptable polymers, waxes, resins and/or proteins. This inner controlling layer is surrounded by an active ingredient layer comprising the pharmaceutically active component.

The pharmaceutical preparation additionally contains an outer controlling layer comprising acrylic copolymers having quaternary ammonium groups and up to 40 weight percent of further pharmaceutically usable polymers. Among a long list of suitable pharmaceutically acceptable polymers to be used as an optional component (meth)acrylate copolymers consisting of 20 to 40 weight percent of methylmethacrylate and 60 to 80 weight percent of methacrylic acid or crosslinked and/or uncrosslinked polyacrylic acid are disclosed. There is no information derivable with respect to the effect or purpose of such acid functional copolymers in the outer controlling layer. Furthermore, since these acid functional copolymers are disclosed as a possible alternative for the optional component in a long list of pharmaceutically acceptable polymers having totally different chemical or physical functionality it is evident that the selection of the acid functional copolymer has no relevance at all for the desired control of release pattern described in these prior art documents.

WO 2006/010394 discloses a medicament in a multilayer form, containing a) a core with a pharmaceutical agent, b) an inner coating, 50 to 95 percent by weight of which are composed of a (co)polymer comprising 95 to 100 percent by weight of radically polymerized vinylic monomers with neutral side groups and 0 to 5 percent by weight of monomers with anionic side groups, c) an outer coating made of a copolymer comprising 75 to 95 percent by weight of radically polymerized $C_1$ to $C_4$ alkyl esters of acrylic acid or methacrylic acid and 5 to 25 percent by weight of (meth)acrylate monomers with an anionic group in the alkyl radical. Said medicament further contains 5 to 30 percent by weight of common pharmaceutical auxiliaries, particularly emollients. Furthermore, the inner coating contains 5 to 50 percent by weight of common pharmaceutical auxiliaries which are not pore-forming agents while the amount of pore-forming agents is less than 5 percent by weight.

DE-A-100 13 029 discloses a pharmaceutical preparation that is especially suitable for drug delivery in the colon. This pharmaceutical preparation comprises:
a) a core containing a pharmaceutically active substance, and
b) an inner controlling layer surrounding the core, comprising a copolymer or a mixture of copolymers of 85 to 98 weight percent of radically polymerizable $C_1$ to $C_4$ alkylesters of acrylic or methacrylic acid, and 15 to 2 weight percent of (meth)acrylate monomers with a quaternary ammonium group in the alkyl radical, and
c) an outer controlling layer comprising a copolymer of 75 to 95 weight percent of radically polymerizable $C_1$ to $C_4$ alkylesters of acrylic or methacrylic acid, and 5 to 25 weight percent of (meth)acrylate monomers with an anionic group in the alkyl radical.

Although it is evident from the experimental data that at a low pH of 1.2 delivery of the drug is retarded until the pH is raised to 7.0 making the pharmaceutical preparation suitable for release in the colon nevertheless a drug release in the colon is incomplete since even after 8 hours only 30 to 80% of the drug is released.

The object of the present invention in view of these prior art documents is to provide a pharmaceutical or nutraceutical preparation for particulate pharmaceutical forms for oral administration for release in the colon showing faster and more complete drug release in the colon.

SUMMARY OF THE INVENTION

The present inventors have surprisingly discovered that by incorporating one or a mixture of a plurality of polymers or copolymers bearing an anionic group or group that can be converted to an anionic group in an inner controlling layer in a pharmaceutical or nutraceutical preparation comprising
a) a core containing a pharmaceutically active substance; and
b) an inner controlling layer surrounding the core comprising one or a mixture of a plurality of (meth)acrylate copolymers bearing a cationic group or a group that can be converted to a cationic group; and
c) an outer controlling layer comprising one or a mixture of a plurality of polymers or copolymers bearing an anionic group or group that can be converted to an anionic group
a pharmaceutical preparation is obtained showing retarded release at low pH but an increased release rate of the pharmaceutically or nutraceutically active substance in the body fluids of the digestive system at neutral pH resulting in a substantially complete release of the active substance in shortened period of time in the colon.

Thus, the defined objective has been attained by a pharmaceutical or nutraceutical preparation comprising
a) a core containing a pharmaceutically or nutraceutically active substance; and
b) an inner controlling layer surrounding the core comprising
  i) one or a mixture of a plurality of (meth)acrylate copolymers bearing a cationic group or a group that can be converted to a cationic group; and ii) one or a mixture of a plurality of polymers or copolymers bearing an anionic group or group that can be converted to an anionic group; and c) an outer controlling layer comprising one or a mixture of a plurality of polymers or copolymers bearing an anionic group or group that can be converted to an anionic group.

PREFERRED EMBODIMENTS ACCORDING TO THE PRESENT INVENTION

Core (a)

In the simplest case, the core can be composed only of the active ingredient but typically additionally comprises a carrier, e.g. a nonpareil, and conventional pharmaceutical excipients that are exemplified by binders, such as cellulose and derivatives thereof, or polyvinyl pyrrolidone (PVP), humectants, disintegration promoters, lubricants, starch and derivatives thereof, polysaccharides, solubilizers; or others.

The core (a) can comprise for example:
pharmaceutically or nutraceutically active components in an amount of 97.5 to 2.5, preferably 80 to 5 weight percent based on the weight of the core;
optionally pharmaceutical excipients in an amount of 0 to 95, preferably 10 to 50 weight percent based on the weight of the core;
optionally a carrier with a proportion of the core weight of 0 to 95, preferably 10 to 60 weight percent.

The cores can be produced, for example by granulation and subsequently compression or direct compression, extrusion and subsequent rounding off, wet or dry granulation or direct pelletizing (e.g. on discs) or by binding of powders (powder layering) onto active ingredient-free beads (nonpareils) or active ingredient-containing particles.

The cores may be pellets with a size of 100 to 1500 μm or may be mini tablets with a size of 1500 to 5000 μm.

The cores may be homogenous or have a layered structure in which case the active ingredient is preferably located in the outer layer.

According to one embodiment of the present invention the core is free of a controlling layer comprising pharmaceutically acceptable polymers, waxes, resins and/or proteins. According to this embodiment such a controlling layer is neither present beneath an active component layer, nor above an active component layer. But the core may optionally comprise sub-coating layers without release controlling functionality. Such coatings are preferably water-soluble and may be applied at very low thickness for example less than 15 μm or less than 10 μm. Suitable materials for such sub-coating layers are water soluble polymers like HPMC or PVP. The function of such sub-coating layers is to avoid incompatibilities of the active ingredient with the controlling layer.

According to a preferred embodiment of the present invention an inactive carrier such as nonpareil is loaded with the active component and optionally with pharmaceutical excipients.

Inner Controlling Layer (b)

The controlling layer (b) contains a combination of (meth)acrylate copolymers bearing a cationic group or group that can be converted to a cationic group and polymers or copolymers having anionic groups and/or groups convertible to anionic groups, and optionally conventional pharmaceutical excipients such as, for example plasticizers, pigments, wetting agents, etc. The controlling layer (b) preferably envelops the core directly without further layers being present between the core and the coating layer. Especially no further controlling layer comprising pharmaceutically acceptable polymers, waxes, resins and/or proteins is positioned between the core (a) and the controlling layer (b). The polymers in the controlling coating (b) are of a film forming type and the coating is converted to a film together with the optionally present excipients to form a continuous coating or coating film. The inner controlling layer (b) in combination with the outer controlling layer (c) in its entirety controls the release of the active component.

The controlling layer (b) according to the present invention comprises preferably component i) in an amount of 50 to 92% more preferred 50 to 80% by weight and component ii) in an amount of 8 to 50%, more preferred 20 to 45% by weight, whereby the weight percentage is based on the total weight of polymers present in the layer.

According to the present invention it is preferred that component i) is an (meth)acrylic copolymer containing quaternary ammonium groups.

Component i)—(Meth)Acrylate Copolymer being a Cationic Group or Groups that can be Converted to a Cationic Group According to one embodiment of the present invention the copolymers according to component i) comprise (meth)acrylate copolymers composed of 80 to 98 weight percent based on the weight of the (meth)acrylic copolymer of structural units derived from $C_1$ to $C_4$ alkyl esters of (meth)acrylic acid and 2 to 20 weight percent based on the weight of the (meth) acrylic copolymer of structural units derived from (meth) acrylate monomers with a quaternary ammonium group in the alkyl radical. The structural units containing a quaternary ammonium group in the alkyl radical that are present in the copolymer according to component i) of the present invention are preferably derived from 2-trimethylammonium ethylmethacrylate chloride.

According to one embodiment of the present invention the copolymers according to component i) comprise (meth)acrylate copolymers composed of 93 to 98 weight percent based on the weight of the (meth)acrylic copolymer of structural units derived from $C_1$ to $C_4$ alkyl esters of (meth)acrylic acid and 2 to 7 weight percent based on the weight of the (meth) acrylic copolymer of structural units derived from (meth) acrylate monomers with a quaternary ammonium group in the alkyl radical (EUTRAGIT® RS-type).

One preferred copolymer to be used as component i) is composed, for example of 50 to 70 weight percent of structural units derived from methylmethacrylate, 20 to 40 weight percent of structural units derived from ethylacrylate and 7 to 2 weight percent of trimethylammonium ethylmethacrylate. A particularly preferred copolymer comprises 65 weight percent of structural units derived from methylmethacrylate, 30 weight percent of structural units of ethylacrylate and 5 weight percent of structural units derived from 2-trimethylammonium ethylmethacrylate chloride. Such copolymers are commercially available as EUDRAGIT® RS.

Another suitable (meth)acrylate copolymer for component i) may be composed, for example of free radically polymerized monomer units of 80 to less than 93 weight percent of $C_1$ to $C_4$ alkyl esters of acrylic or (meth)acrylic acid and more than 7 to 20 weight percent of (meth)acrylate monomers having a quaternary ammonium group in the alkyl radical, preferably 85 to less than 93 weight percent of $C_1$ to $C_4$ alkyl esters of acrylic or (meth)acrylic acid and more than 7 to 15 weight percent of (meth)acrylate monomers having a quaternary ammonium group in the alkyl radical. Such (meth)acrylate copolymers are commercially available and have been used for a long time for release slowing coatings (EUDRAGIT® RL-type).

A specifically suitable copolymer comprises, for example 60 weight percent methylmethacrylate, 30 weight percent ethylacrylate and 10 weight percent of 2-trimethylammonium ethylmethacrylate chloride (EUDRAGIT® RL).

According to a particularly preferred embodiment of the present invention the copolymers according to component i) comprise a mixture of
- 40 to 99 weight percent based on the total weight of the mixture of (meth)acrylate copolymers composed of 93 to 98 weight percent based on the weight of the (meth)acrylic copolymer of structural units derived from $C_1$ to $C_4$ alkyl esters of (meth)acrylic acid and 2 to 7 weight percent based on the weight of the (meth)acrylic copolymer of structural units derived from (meth)acrylate monomers with a quaternary ammonium group in the alkyl radical; and
- 1 to 60 weight percent based on the total weight of the mixture of (meth)acrylate copolymers composed of 85 to less than 93 weight percent based on the weight of the (meth)acrylic copolymer of structural units derived from $C_1$ to $C_4$ alkyl esters of (meth)acrylic acid and more than 7 to 15 weight percent based on the weight of the (meth)acrylic copolymer of structural units derived from (meth)acrylate monomers with a quaternary ammonium group in the alkyl radical.

In the mixture the first component as defined above may be selected from the EUDRAGIT® RS-type copolymers including the preferred embodiment as defined above. The proportion of the EUDRAGIT® RS-type copolymers is 40-99, preferably 60 to 95 weight percent based on the total weight of the mixture of (meth)acrylate copolymers according to component i). Particularly preferred is a range of 70 to 90 weight percent.

A suitable (meth)acrylate copolymer for the second component of the mixture may be selected from (meth)acrylate copolymers of the EUDRAGIT® RL-type as described above. The proportion in the mixture can be up to 60 weight percent, preferably 5 to 40 weight percent, more preferred 10 to 30 weight percent based on the total amount of acrylic copolymers having quaternary ammonium groups.

Component ii) Polymers or Copolymers Containing Anionic Groups or Groups that are Convertible to an Anionic Group Furthermore, the controlling layer (b) comprises as component ii) polymers or copolymers containing anionic groups or groups that are convertible to an anionic group that are preferably selected from carboxyl functional (meth)acrylic polymers or copolymers and carboxyl functional polysaccharides and products of at least partial neutralization thereof.

Suitable carboxyl functional polysaccharides or products of at least partial neutralization thereof may be selected from sodium alginate, carboxymethyl cellulose and its salts (CMC, Na-CMC, Blanose, Tylopur), carboxymethylethyl cellulose and its salts, cellulose acetate phthalate (CAP), cellulose acetate succinate (CAS), cellulose acetate trimelliate (CAT), hydroxypropyl methyl cellulose phthalate (HPMCP, HP50, HP55), hydroxypropylmethyl cellulose acetate succinate (HPMCAS-LF, -MF, -HF).

Other suitable carboxyl functional copolymers are vinyl copolymers comprising structural units that are derived from unsaturated carboxylic acids other than acrylic acid or methacrylic acid as exemplified by polyvinylacetatephthalate or a copolymer of vinylacetate and crotonic acid 9:1.

According to a preferred embodiment of the present invention the polymers or copolymers of component ii) are selected from carboxyl functional (meth)acrylic polymers or copolymers and products of at least partial neutralization thereof.

Suitable carboxyl functional (meth)acrylic copolymers are selected from (meth)acrylate copolymers composed of 5 to 85% by weight of structural units containing a carboxyl group and of 95 to 15% by weight of structural units derived from alkyl esters, preferably C1-C4 alkyl esters of (meth)acrylic acid, whereby the percentages are based on the weight of the copolymer.

Preferably the structural units containing a carboxyl group are derived from acrylic acid or methacrylic acid.

The structural units containing a group that is convertible to an anionic group may be partially or fully neutralized for instance by alkali or ammonia ions.

Depending on the degree of neutralization of acid functional (meth)acrylic copolymer the carboxylic groups are fully or partially converted to the anionic carboxylate group. Preferably the degree of partially neutralization is not more than 15 mol-%, not more than 12 mol-%, not more than 10 mol-%, not more than 8 mol-%. It is most preferred if the structural units derived from acrylic acid or methacrylic acid are not neutralized.

$C_1$- to $C_4$-alkyl esters of acrylic or methacrylic acid are in particular methyl methacrylate, ethyl methacrylate, butyl methacrylate, methyl acrylate, ethyl acrylate and butyl acrylate.

The proportions mentioned normally add up to 100% by weight. However it is also possible in addition, without this leading to an impairment or alteration of the essential properties, for small amounts in the region of 0 to 10, for example 1 to 5, % by weight of further monomers capable of vinylic copolymerization, such as, for example, hydroxyethyl methacrylate or hydroxyethyl acrylate, vinylpyrrolidone, vinylmalonic acid, styrene, vinyl alcohol, vinyl acetate and/or derivatives thereof, to be present. It is preferred that no further monomers capable of vinylic copolymerization are present.

According to a particularly preferred embodiment the component ii) of the controlling layer (b) is composed of 41 to 60 weight percent based on the weight of the copolymer of structural units derived from methylmethacrylate or ethylacrylate and 40 to 59 weight percent based on the weight of the copolymer of structural units derived from (meth)acrylic acid whereby the carboxyl functional groups on the copolymer can be fully or partially neutralized.

Following examples of (meth)acrylic copolymers are suitable as component ii) in the controlling layer (b).

EUDRAGIT® L is a copolymer of 50% by weight methyl methacrylate and 50% by weight methacrylic acid. The pH of the start of the specific active ingredient release in intestinal juice or simulated intestinal fluid can be stated to be pH 6.0.

EUDRAGIT® L 100-55 is a copolymer of 50% by weight ethyl acrylate and 50% by weight methacrylic acid. EUDRAGIT® L 30 D-55 is a dispersion comprising 30% by weight EUDRAGIT® L 100-55. The pH of the start of the specific active ingredient release in intestinal juice or simulated intestinal fluid can be stated to be pH 5.5.

Likewise suitable are anionic (meth)acrylate copolymers composed of 20 to 40% by weight methacrylic acid and 80 to 60% by weight methyl methacrylate (EUDRAGIT® S type). The pH of the start of the specific active ingredient release in intestinal juice or simulated intestinal fluid can be stated to be pH 7.0.

Suitable (meth)acrylate copolymers are those consisting of 10 to 30% by weight methyl methacrylate, 50 to 70% by weight methyl acrylate and 5 to 15% by weight methacrylic acid (EUDRAGIT® FS type). The pH at the start of the specific active ingredient release in intestinal juice or simulated intestinal fluid can be stated to be pH 7.0.

EUDRAGIT® FS is a copolymer of 25% by weight methyl methacrylate, 65% by weight methyl acrylate and 10% by weight methacrylic acid. EUDRAGIT® FS 30 D is a dispersion comprising 30% by weight EUDRAGIT® FS.

Additionally suitable is a copolymer composed of
20 to 34% by weight methacrylic acid and/or acrylic acid,
20 to 69% by weight methyl acrylate and
0 to 40% by weight ethyl acrylate and/or where appropriate
0 to 10% by weight further monomers capable of vinylic copolymerization, with the proviso that the glass transition temperature of the copolymer according to ISO 11357-2, subsection 3.3.3, is not more than 60° C. This (meth)acrylate copolymer is particularly suitable, because of its good elongation at break properties, for compressing pellets to tablets.

Additionally suitable is a copolymer composed of
20 to 33% by weight methacrylic acid and/or acrylic acid,
5 to 30% by weight methyl acrylate and
20 to 40% by weight ethyl acrylate and
more than 10 to 30% by weight butyl methacrylate and where appropriate
0 to 10% by weight further monomers capable of vinylic copolymerization,
where the proportions of the monomers add up to 100% by weight, with the proviso that the glass transition temperature of the copolymer according to ISO 11357-2, subsection 3.3.3 (midpoint temperature $T_{mg}$), is 55 to 70° C. Copolymers of this type are particularly suitable, because of its good mechanical properties, for compressing pellets to tablets.

The abovementioned copolymer is composed in particular of free-radical polymerized units of
20 to 33, preferably 25 to 32, particularly preferably 28 to 31% by weight methacrylic acid or acrylic acid, with preference for methacrylic acid,
5 to 30, preferably 10 to 28, particularly preferably 15 to 25% by weight methyl acrylate,
20 to 40, preferably 25 to 35, particularly preferably 18 to 22% by weight ethyl acrylate, and
more than 10 to 30, preferably 15 to 25, particularly preferably 18 to 22% by weight butyl methacrylate,
where the monomer composition is chosen so that the glass transition temperature of the copolymer is from 55 to 70° C., preferably 59 to 66, particularly preferably 60 to 65° C.

Glass transition temperature means in this connection in particular the midpoint temperature $T_{mg}$ according to ISO 11357-2, subsection 3.3.3. Measurement takes place without added plasticizer, with residual monomer contents (REMO) of less than 100 ppm, with a heating rate of 10° C./min and under a nitrogen atmosphere.

The anionic (meth)acrylate copolymers can be prepared in a manner known per se by free-radical polymerization of the monomers (see, for example, EP 0 704 207 A2 and EP 0 704 208 A2). The copolymer according to the invention can be prepared in a manner known per se by free-radical emulsion polymerization in aqueous phase in the presence of, preferably, anionic emulsifiers, for example by the process described in DE-C 2 135 073.

The copolymer can be prepared by conventional processes of free-radical polymerization continuously or discontinuously (batch processes) in the presence of free-radical forming initiators and, where appropriate, regulators to adjust the molecular weight undiluted, in solution, by bead polymerization or in emulsion. The average molecular weight Mw (weight average, determined for example by measuring the solution viscosity) may be for example in the range from 80 000 to 1 000 000 (g/mol). Emulsion polymerization in aqueous phase in the presence of water-soluble initiators and (preferably anionic) emulsifiers is preferred.

In the case of bulk polymerization, the copolymer can be obtained in solid form by crushing, extrusion, granulation or hot cut.

The (meth)acrylate copolymers are obtained in a manner known per se by free-radical bulk, solution, bead or emulsion polymerization. They must before processing be brought to the particle size range of the invention by suitable grinding, drying or spraying processes. This can take place by simple crushing of extruded and cooled pellets or hot cut.

The use of powders may be advantageous especially on mixture with other powders or liquids. Suitable apparatuses for producing powders are familiar to the skilled person, e.g. air jet mills, pinned disc mills, compartment mills. It is possible where appropriate to include appropriate sieving steps. A suitable mill for industrial large quantities is, for example, an opposed jet mill (Multi No. 4200) operated with a gauge pressure of about 6 bar.

Bases suitable for the at least partial neutralization of the anionic (meth)acrylic copolymers of the invention are those expressly mentioned in EP 0 088 951 A2 or WO 2004/096185 or derivable therefrom. The following bases are suitable in particular: sodium hydroxide solution, potassium hydroxide solution (KOH), ammonium hydroxide or organic bases such as, for example, triethanolamine, sodium carbonate, potassium carbonate, sodium bicarbonate, trisodium phosphate, trisodium citrate or ammonia or physiologically tolerated amines such as triethanolamine or tris(hydroxymethyl)aminomethane.

Further suitable cationic, organic bases are basic amino acids histidine, arginine and/or lysine.

Outer Controlling Layer c)

The outer controlling layer c) comprises one or a mixture of a plurality of polymers or copolymers bearing an anionic group or group that can be converted to an anionic group.

Generally the same polymers or copolymers bearing an anionic group or group that can be converted to an anionic group as described above with respect to component ii) of the inner controlling layer b) including all specific embodiments to are likewise suitable for the outer controlling layer c).

Particularly suitable for the outer controlling layer c) are copolymers composed of 60 to 95% by weight, preferably 85 to 95% by weight based on the weight of the copolymer of structural units derived from methyl methacrylate or ethyl acrylate and 5 to 40% by weight, preferably 5 to 15% by weight based on the weight of the copolymer of structural units derived from acrylic or methacrylic acid. The copolymers may be at least partial neutralized. Particularly preferred are copolymers according to the EUDRAGIT® FS type especially EUDRAGIT® FS.

Further Pharmaceutically Usual Excipients

The core and/or the coating may comprise further pharmaceutically usual excipients. Further additives, in particular as processing aids, are intended to ensure a reliable and reproducible production process and good long-term storage stability. They may influence the permeability of the coatings which can be utilized where appropriate as additional control parameters. As discussed above the pharmaceutical excipients which may be present in the core in addition to the pharmaceutically active component may be, for example binders, such as cellulose and derivatives thereof, polyvinyl pyrrolidone (PVP), gelatin, (meth)acrylates, starch and derivatives thereof, or sugars.

Plasticizers:

Plasticizers may be present, in particular in the coating or in the (meth)acrylic copolymers of the coating. Substances suitable as plasticizers usually have a molecular weight of between 100 and 20,000 and comprise one or more hydrophilic groups in the molecule, e.g. hydroxyl, ester or ammonium groups. They are frequently esters which are liquid at room temperature, such as citrates, phthalates, sebacates or castor oil. Examples of suitable plasticizers are alkyl citrates, e.g. triethyl citrate, glycerol esters, alkyl phthalates, alkyl sebacates, sucrose esters, sorbitan esters, diethyl sebacate, dibutyl sebacate and polyethylene glycols with a molecular weight of 4,000 to 20,000. Preferred plasticizers are triethyl citrate and acetyl triethyl citrate. The plasticizers may be present, for example in amounts of from 5 to 25 weight percent based on the polymers of the coating.

Non-Sticking Agents:

These substances which usually have lipophilic properties, can be added to the spray suspensions and prevent agglomeration of the cores during the film coating. It is possible to employ, for example talc, silica, kaolin, magnesium stearate or calcium stearate or non-ionic emulsifiers with an HLB of between 3 and 8, like glycerol monostearate. The usual amounts employed are between 0.5 to 100 weight percent based on the weight of the cores. The non-sticking agents may alternatively employed in the coating, preferably in an amount of 0.5 to 100 weight percent based on the total weight of the polymers in the coating.

Further Excipients:

Further pharmaceutically usual excipients which can be added in a manner known per se are, for example, pharmaceutically acceptable stabilizers, colorants, antioxidants, wetting agents, pore formers, pigments, gloss agents, etc.

Pharmaceutically Active Components

The multilayer pharmaceutical form of the invention is suitable in principle for any pharmaceutically active components. Medicinal substances in use can be found in reference works such as, for example, the Rote Liste or the Merck Index.

The active components or medicinal substances employed for the purposes of the invention are intended to be used on or in the human or animal body in order 1. to cure, to alleviate, to prevent or to diagnose disorders, conditions, physical damage or pathological symptoms;
2. to reveal the condition, the status or the functions of the body or mental states;
3. to replace active substances or body fluids produced by the human or animal body;
4. to ward off, to eliminate or to render harmless pathogens, parasites or exogenous substances, or
5. to influence the condition, the status or the functions of the body or mental states.

These pharmaceutically active substances may belong to one or more active ingredient classes such as ACE inhibitors, adrenergics, adrenocorticosteroids, acne therapeutic agents, aldose reductase inhibitors, aldosterone antagonists, alpha-glucosidase inhibitors, alpha 1 antagonists, remedies for alcohol abuse, amino acids, amoebicides, anabolics, analeptics, anaesthetic additions, anaesthetics (non-inhalational), anaesthetics (local), analgesics, androgens, angina therapeutic agents, antagonists, antiallergics, antiallergics such as PDE inhibitors, antiallergics for asthma treatment, further antiallergics (e.g. leukotriene antagonists, antianaemics, antiandrogens, antianxiolytics, antiarthritics, antiarrhythmics, antiatheriosclerotics, antibiotics, anticholinergics, anticonvulsants, antidepressants, antidiabetics, antidiarrhoeals, antidiuretics, antidotes, antiemetics, antiepileptics, antifibrinolytics, antiepileptics, antihelmintics, antihistamines, antihypotensives, antihypertensives, antihypertensives, antihypotensives, anticoagulants, antimycotics, antiestrogens, antiestrogens (non-steroidal), antiparkinson agents, antiinflammatory agents, antiproliferative active ingredients, antiprotozoal active ingredients, antirheumatics, antischistosomicides, antispasmolytics, antithrombotics, antitussives, appetite suppressants, arteriosclerosis remedies, bacteriostatics, beta-blockers, beta-receptor blockers, bronchodilators, carbonic anhydrase inhibitors, chemotherapeutic agents, choleretics, cholinergics, cholinergic agonists, cholinesterase inhibitors, agents for the treatment of ulcerative colitis, cyclooxygenaze inhibitors diuretics, ectoparasiticides, emetics, enzymes, enzyme inhibitors, enzyme inhibitors, active ingredients to counter vomiting, fibrinolytics, fungistatics, gout remedies, glaucoma therapeutic agents, glucocorticoids, glucocorticosteroids, haemostatics, cardiac glycosides, histamine H2 antagonists, hormones and their inhibitors, immunotherapeutic agents, cardiotonics, coccidiostats, laxatives, lipid-lowering agents, gastrointestinal therapeutic agents, malaria therapeutic agents, migraine remedies, microbiocides, Crohn's disease, metastasis inhibitors, migraine remedies, mineral preparations, motility-increasing active ingredients, muscle relaxants, neuroleptics, active ingredients for treatment of estrogens, osteoporosis, otologicals, antiparkinson agents, phytopharmaceuticals, proton pump inhibitors, prostaglandins, active ingredients for treating benign prostate hyperblasia, active ingredients for treating pruritus, psoriasis active ingredients, psychoactive drugs, free-radical scavengers, renin antagonists, thyroid therapeutic agents, active ingredients for treating seborrhoea, active ingredients to counter seasickness, spasmolytics, alpha- and beta-sympathomimetics, platelet aggregation inhibitors, tranquilizers, ulcer therapeutic agents, further ulcer therapeutic agents, agents for the treatment of urolithiasis, virustatics, vitamins, cytokines, active ingredients for combination therapy with cytostatics, cytostatics.

Examples of suitable active components are acarbose, acetylsalicylic acid, abacavir, aceclofenac, aclarubicin, acyclovir, actinomycin, adalimumab, adefovir, adefovirdipivoxil, adenosylmethionine, adrenaline and adrenaline derivatives, agalsidase alpha, agalsidase beta, alemtuzumab, almotriptan, alphacept, allopurinol, almotriptan, alosetron, alprostadil, amantadine, ambroxol, amisulpride, amlodipine, amoxicillin, 5-aminosalicylic acid, amitriptyline, amlodipine, amoxicillin, amprenavir, anakinra, anastrozole, androgen and androgen derivatives, apomorphine, aripiprazole, arsenic trioxide, artemether, atenolol, atorvastatin, atosiban, azathioprine, azelaic acid, barbituric acid derivatives, balsalazide, basiliximab, beclapermin, beclomethasone, bemiparin, benzodiazepines, betahistine, bexaroten, bezafibrate, bicalutamide, bimatoprost, bosentan, botulinus toxim, brimonidine, brinzolamide, budesonide, budipine, bufexamac, bumetanide, buprenorphine, bupropion, butizine, calcitonin, calcium antagonists, calcium salts, candesartan, capecitabine, captopril, carbamazepine, carifenacin, carvedilol, caspofungin, cefaclor, cefadroxil, cefalexin cefalosporins, cefditoren, cefprozil, celecoxib, cepecitabine, cerivastatim, cetirizine, cetrorelix, cetuximab, chenodeoxycholic acid, chorionic gonadotropin, ciclosporin, cidofovir, cimetidine, ciprofloxacin, cisplatin, cladribine, clarithromycin, clavulanic acid, clindamycin, clobutinol, clonidine, clopidogrel, codeine, caffeine, colestyramine, cromoglicic acid, cotrimoxazole, coumarin and coumarin derivatives, darbepoetin, cysteamine, cysteine, cytarabine, cyclophosphamide, cyproterone, cytarabine, daclizumab, dalfopristin, danaparoid, dapiprazole, darbepoetin, defepripone, desipramine, desirudin, desloaratadine, desmopressin, desogestrel, desonide, dexibuprofen, dexketoprofen, disoproxil, diazepam and diazepam derivatives, dihydralazine, diltiazem, dimenhydrinate, dimethyl sulphoxide, dimeticon, dipivoxil, dipyridarnoi, dolasetron, domperidone, and domperidane derivatives, donepzil, dopamine, doxazosin, doxorubizin, doxylamine, diclofenac, divalproex, dronabinol, drospirenone, drotrecogin alpha, dutasteride, ebastine, econazole, efavirenz, eletripan, emidastine, emtricitabine, enalapril, encepur, entacapone, enfurvirtide, ephedrine, epinephrine, eplerenone, epoetin and epoetin derivatives, eprosartan, eptifibatide, ertapenem, esomeprazole, estrogen and estrogen derivatives, etanercept, ethenzamide, ethinestradiol, etofenamate, etofibrate, etofylline, etonogestrel, etoposide, exemestan, exetimib, famciclovir, famotidine, faropenan daloxate, felodipine, fenofibrate, fentanyl, fenticonazole, fexofenadine, finasteride, fluconazole, fludarabine, flunarizine, fluorouracil, fluoxetine, flurbiprofen, flupirtine, flutamide, fluvastatin, follitropin, fomivirsen, fondaparinux, formoterol, fosfomicin, frovatriptan, furosemide, fusidic acid, gadobenate, galantamine, gallopamil, ganciclovir, ganirelix, gatifloxacin, gefitinib, gemfibrozil, gentamicin, gepirone, progestogen and progestogen derivatives, ginkgo, glatiramer, glibenclamide, glipizide, glucagon, glucitol and glucitol derivatives, glucosamine and glucosamine derivatives, glycoside antibiotics, glutathione, glycerol and glycerol derivatives, hypothalamus hormones, goserelin, grepafloxacin, gyrase inhibitors, guanethidine, gyrase inhibitors, haemin, halofantrine, haloperidol, urea derivatives as oral antidiabetics, heparin and heparin derivatives, cardiac glycosides, hyaluronic acid, hydralazine, hydrochlorothiazide and hydrochlorothiazide derivatives, hydroxyomeprazole, hydroxyzine, ibritumomab, ibuprofen, idarubicin, ifliximab, ifosfamide, iloprost, imatinib, imidapril, imiglucerase, imipramine, imiquimod, imidapril, indometacin, indoramine, infliximab, insulin, insulin glargin, interferons, irbesartan, irinotecan, isoconazole, isoprenaline, itraconazole, ivabradines, iodine and iodine derivatives, St. John's wort, potassium salts, ketoconazole, ketoprofen, ketotifen, lacidipine, lansoprazole, laronidase, latanoprost, leflunomide, lepirudin, lercanidipine, leteprinim, letrozole, levacetylmethadol, levetiracetam, levocetirizine, levodopa, levodrpropicin, levomethadone, licofelone, linezolide, lipinavir, lipoic acid and lipoic acid derivatives, lisinopril, lisuride, lofepramine, lodoxamide, lomefloxacin, lomustine, loperamide, lopinavir, loratadine, lornoxicam, losartan, lumefantrine, lutropine, magnesium salts, macrolide antibiotics, mangafodipir, maprotiline, mebendazole, mebeverine, meclozine, mefenamic acid, mefloquine, meloxicam, memantine, mepindolol, meprobamate, meropenem, mesalazine, mesuximide, metamizole, metformin, methadone, methotrexate, methyl 5-amino-4-oxopentanoate, methylnaloxone, methylnaloxone, methylnaltrexones, methylphenidate, methylprednisolone, metixen, metoclopramide, metoprolol, metronidazole, mianserin, mibefradil, miconazole, mifepristone, miglitol, miglustad, minocycline, minoxidil, misoprostol, mitomycin, mizolastine, modafinil, moexipril, montelukast, moroctocog, morphinans, morphine and morphine derivatives, moxifloxacin, ergot alkaloids, nalbuphine, naloxone, naproxen, naratriptan, narcotine, natamycin, nateglinide, nebivolol, nefazodone, nelfinavir, neostigmine, neramexan, nevirapine, nicergoline, nicethamide, nifedipine, niflumic acid, nimodipine, nimorazole, nimustine, nesiritide, nisoldipine, norfloxacin, novamine sulphone, noscapine, nystatin, ofloxacin, oktotride, olanzapine, olmesartan, ondansetron, orlistat, oseltamivir, omeprazole, omoconazole, ondansetron, orlistat, oseltamivir, oxaceprol, oxacillin, oxaliplatin, oxaprozin, oxcarbacepin, oxicodone, oxiconazole, oxymetazoline, palivizumab, palanosetron, pantoprazole, paracetamol, parecoxib, paroxetine, pegaspargase, peginterferon, pegfilgrastrim, penciclovir, oral penicillins, pentazocine, pentifylline, pentoxifylline, peptide antibiotics, perindopril, perphenazine, pethidine, plant extracts, phenazone, pheniramine, phenylbutyric acid, phenyloin, phenothiazines, phenserine, phenylbutazone, phenyloin, pimecrolimus, pimozide, pindolol, pioglitazone, piperazine, piracetam, pirenzepine, piribedil, pirlindol, piroxicam, pramipexol, pramlintide, pravastatin, prazosin, procaine, promazine, propiverine, propranolol, propionic acid derivatives, propyphenazone, prostaglandins, protionamide, proxyphylline, quetiapine, quinapril, quinaprilate, quinupristine, ramipril, ranitidine, rabeprazole, raloxifen, ranolazine, rasburicase, reboxetin, repaclinides, reproterol, reserpine, revofloxacin, ribavirin, rifampicin, riluzoles, rimexolone, risedronate, risperidone, ritonavir, rituximab, rivastimen, risatriptan, rofecoxib, ropinirol, ropivacaine, rosiglitazone, roxatidine, roxithromycin, ruscogenin, rosuvastatin, rutoside and rutoside derivatives, sabadilla, salbutamol, salicylates, salmeterol, saperconazoles, thyroid hormones, scopolamine, selegiline, sertaconazole, sertindole, sertraline, sevelamer, sibutramine, sildenafil, silicates, simvastatin, sirolimus, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulphasalazine, sulpiride, sultamicillin, sultiam, sumatriptan, suxamethonium chloride, tacrine, tacrolimus, tadalafil, taliolol, talsaclidine, tamoxifen, tasonermin, tazarotene, tegafur, tegaserod, telithromycin, telmisartan, temoporfin, temozolomide, tenatoprazole, tenecteplase, teniposide, tenofovir, tenoxicam, teriparatide, terazosin, terbinafine, terbutaline, terfenadine, teriparatide, terlipressin, tertatolol, testosterone and testosterone derivatives, tetracyclines, tetryzoline, tezosentan, theobromine, theophylline, theophylline derivatives, thiamazole, thiotepa, thr. growth factors, tiagabine, tiapride, tibolone, ticlopidine, tilidine, timolol, tinidazole, tioconazole, tioguanine, tiotropium, tioxolone, tirazetam, tiropramide, trofiban, tizanidine, tolazoline, tolbutamide, tolcapone, tolnaftate, tolperisone, tolterodine, topiramate, topotecan, torasemide, tramadol, tramazoline, trandolapril, tranylcypromine, trapidil, trastuzumab, travoprost, trazodone, trepostinil, triamcinolone and triamcinolone derivatives, triamterene, trifluperidol, trifluridine, trimetazidines, trimethoprim, trimipramine, tripelennamine, triprolidine, trifosfamide, tromantadine, trometamol, tropalpine, trovafloxacin, troxerutin, tulobuterol, trypsins, tyramine, tyrothricin, urapidil, ursodeoxycholic acid, theophylline ursodeoxycholic acid, valaciclovir, valdecoxib, valganciclovir, valproic acid, valsartan, vancomycin, vardenafil, vecuronium chloride, venlafaxine, verapamil, verteporfin, vidarabine, vigabatrine, viloxazine, vinblastine, vincamine, vincristine, vindesine, vinorelbine, vinpocetine, viquidil, vitamin D and derivatives of vitamin D, voriconazole, warfarin, xantinol nicotinate, ximelagatran, xipamide, zafirlukast, zalcitabine, zaleplon, zanamivir, zidovudine, ziprasidone, zoledronic acid, zolmitriptan, zolpidem, zoplicone, zotepine and the like.

The active components can, if desired, also be used in the form of their pharmaceutically acceptable salts or derivatives, and in the case of chiral active ingredients it is possible to employ both optically active isomers and racemates or mixtures of diastereomers. If desired, the compositions of the invention may also comprise two or more active pharmaceutical ingredients.

Nutraceuticals

Nutraceuticals can be defined as extracts of foods claimed to have medical effects on human health. The nutraceutical is usual contained in a medical format such as capsule, tablet or powder in a prescribed dose. Examples for nutraceuticals are resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flavonoids, antioxidants, alpha-linoleic acid from flax seed, beta-carotene from marigold petals or antocyanins from berries. Sometimes the expression neutraceuticals is used as synonym for nutraceuticals.

Application of the Controlling Layers b) and c)

The application process may be selected from spray application from organic solutions or aqueous dispersions, or melting or direct powder application. It is essential for implementation in this case that a uniform pore-free coating is produced. Although application of aqueous dispersions is preferred compared to organic solutions, especially in countries where strict VOC requirements have to be met, it is also possible to apply the coating application by using an organic solution.

Suitable application processes can be found, for example, in Bauer, K. H., Lehmann, K., Osterwald, H. P. Rothgang, G. "*Coated Pharmaceutical Dosage Forms*", 1998, Wissenschaftliche Verlagsgesellschaft mbH, Stuttgart and CRC Press LLC, Boca Raton, Fla., USA or McGinity, J. W., "*Aqueous Polymeric Coatings for Pharmaceutical Dosage Forms*, Second Edition, Revised and Expanded", 1997, Marcel Dekker Inc., New York, USA.

Relevant properties, required tests and specifications for the application are listed in pharmacopoeias.

Details are to be found in customary textbooks, e.g.:
Voigt, R. (1984), Lehrbuch der pharmazeutischen Technologie; Verlag Chemie Weinheim—Beerfield Beach/Fla. —Basle.
Sucker, H., Fuchs, P., Speiser, P.: Pharmazeutische Technologie, Georg Thieme Verlag Stuttgart (1991), especially Chapters 15 and 16, pp. 626-642.
Gennaro, A., R. (Editor), Remington's Pharmaceutical Sciences, Mack Publishing Co., Easton Pa. (1985), Chapter 88, pp. 1567-1573.
List, P. H. (1982): Arzneiformenlehre, Wissenschaftliche Verlagsgesellschaft mbH, Stuttgart.

Amounts and Relations of the Controlling Layers

The controlling layer (b) is preferably applied to the core in an amount to result in a total weight of controlling layer (b) from 2.5 to 100, preferably 10 to 70, particularly preferred 15 to 40 weight percent based on the total weight of core (a).

The outer coating (c) is preferably applied onto the controlling layer (b) in an amount to result in a total weight of the outer layer (c) from 5 to 100, preferably 10 to 80, particularly preferred from 15 to 50 weight percent based on the total weight of the core (a) and the inner coating (b). For instance the thickness of the inner coating layer (b) can be about 10-50 μm. The outer coating layer (c) may have a thickness of 20-100 μm. As a rule the outer layer (c) is thicker than the inner coating layer (b).

Topcoats

The pharmaceutical or nutraceutical preparation of the present invention may optionally comprise a topcoat that does not have any release controlling functionality. Preferably the topcoat is a water-soluble layer that functions as carrier for pigments or lubricants. A suitable topcoat material may be selected from polysaccharides.

Administration Forms

It is in principle possible for the pharmaceutical or nutraceutical preparations according to the present invention to be used directly by oral administration. However, further processing steps preferably follow in a manner known for producing pharmaceutical forms. The preparation may be present, for example in colored form which can be processed by means of pharmaceutically usual excipients, and in a manner known per se to multiparticulate pharmaceutical forms, in particular to pellet containing tablets, mini-tablets, capsules, sachets or reconstitutable powders.

The preparation according to the present invention can preferably be compressed in the form of pellets, for example to give a tablet. Alternatively the preparation can, for example also be in the form of pellets or mini-tablets which are introduced into a gelatin capsule or HPMC (Methylose) capsule and enveloped thereby.

EXAMPLES

Copolymers

The following copolymers were used in the Examples.
Copolymer 1:
Copolymer 1 is composed of 65 weight percent of methyl methacrylate, 30 weight percent of ethyl acrylate and 5 weight percent 2-trimethylammoniumethyl methacrylate chloride (EUDRAGIT® RS). The copolymer is applied from a 30% aqueous dispersion (EUDRAGIT® RS 30D).
Copolymer 2:
Copolymer 2 is composed of 60 weight percent of methyl methacrylate, 30 weight percent of ethyl acrylate and 10 weight percent 2-trimethylammoniumethyl methacrylate chloride (EUDRAGIT® RL). The copolymer is applied from a 30% aqueous dispersion (EUDRAGIT® RL 30D).
Copolymer 3:
Copolymer 3 is composed of 50 weight percent of methyl methacrylate and 50 weight percent methacrylic acid (EUDRAGIT® L) used without neutralization. The copolymer is applied from solid polymer (EUDRAGIT L100) that is suspended in water.
Copolymer 4:
Copolymer 4 is composed of 25% by weight methyl methacrylate, 65% by weight methyl acrylate and 10% by weight methacrylic acid (EUDRAGIT® FS) used without neutralization. The copolymer is applied from a 30% aqueous dispersion (EUDRAGIT® FS 30D).
Methods
Model Drug
Studies were conducted using Mesalamin (5-ASA) as a model drug.
Excipients
All excipients were used in pharmaceutical quality
Dissolution Studies
Coated pellets were tested according to
USP 28-NF23, General Chapter <711>, *Dissolution*,
Dissolution Parameters:
Apparatus: USP Type-I (Basket)
RPM: 100/min.
Temperature: 37.5±0.5° C.
Dissolution volume: 900 ml.
Withdrawal volume: 5 ml withdrawn manually using pipette, without replenishment of the medium.
Withdrawal interval: initial, 1.0 Hr, 2.0 Hr, 3.0 Hr, 4.0 Hr, 5.0 Hr, 6.0 Hr, 7.0 Hr, 8.0 Hr, 10.0 Hr, 11.0 Hr and 12.0 Hr.
Mode of detection: HPLC Dissolution Medium 1:
 0.1 molar Hydrochloric acid (HCl), (European Pharmacopoeia=EP)
Dissolution Medium 2:
 Phosphate buffer pH 7.5 (European Pharmacopoeia=EP)
Formulation Details
 Cores (sugar sphere etc.) of 355-500 microns were loaded with Mesalamine in a fluidised bed processor using bottom spray. Polyvinyl pyrrolidone was used as a binder.
Coating Suspension Preparation:
 EUDRAGIT® dispersions are mixed in a suitable vessel applying gentle stirring. Lubricants and different polymers are dissolved or dispersed in water applying high shear forces.
 The lubricant suspension is poured into the EUDRAGIT® dispersion applying gentle stirring. Stirring is continued through the entire coating process.
Coating Process:
 Drug layered pellets were coated with different coating suspensions in a fluidized bed apparatus under appropriate conditions, i.e. a spray rate of approximately 20 g/min coating suspension per kg cores and a bed temperature of approximately 25-28° C. After coating the pellets were fluidised at 50° C. for one hour in a fluid bed processor.
 In Table 1 the compositions are given in weight percent on a dry basis.

TABLE 1

| Sr. No. | Ingredients | Example 1 (comparative) | Example 2 | Example 3 |
|---|---|---|---|---|
| | Core | | | |
| 1. | Non pareil seeds (355-500 μm) | 16.27 | 15.96 | 15.57 |
| 2. | Mesalamine | 63.14 | 61.91 | 60.40 |
| 3. | Aerosil 200[1] | 0.65 | 0.64 | 0.62 |
| 4. | Povidone(PVP-K30) | 2.78 | 2.74 | 2.59 |
| | Inner controlling layer | | | |
| 5. | Copolymer 1 | 3.98 | 3.90 | 3.80 |
| 6. | Copolymer 2 | 2.65 | 2.60 | 2.53 |
| 7. | Glyceryl monostearate | 0.74 | 0.73 | 0.72 |
| 8. | Triethyl citrate | 1.33 | 1.30 | 1.27 |
| 9. | Copolymer 3 | — | 1.95 | 4.43 |
| | Outer controlling layer | | | |
| 10 | Copolymer 4 | 8.29 | 8.12 | 7.92 |
| 11 | Tween 80[2] | 0.17 | 0.16 | 0.16 |

[1]Aerosil 200 = colloidal silica, pharmaceutical quality, average particle size about 12 nm
[2]Tween 80 = (polysorbate 80, pharmaceutical quality)

The pharmaceutical formulations according to Examples 1 to 3 were analysed for drug release in 0.1 molar HCl for the first two hours, followed by phosphate buffered saline pH 7.5 for the remaining time.
The results are summarized in Table 2.

TABLE 2

| Time in hr. | Example 1 | Example 2 | Example 3 |
|---|---|---|---|
| 0.00 | 0.00 | 0.00 | 0.00 |
| 1.00 | 0.19 | 0.19 | 0.99 |
| 2.00 | 0.46 | 0.53 | 3.19 |
| 3.00 | 20.64 | 31.88 | 36.54 |
| 4.00 | 31.83 | 53.98 | 62.87 |
| 5.00 | 41.01 | 69.95 | 80.12 |
| 6.00 | 49.26 | 81.30 | 91.99 |
| 7.00 | 57.19 | 88.39 | 95.94 |
| 8.00 | 63.36 | 93.40 | 97.62 |
| 10.00 | 74.75 | 94.99 | |
| 11.00 | 79.78 | 94.62 | |
| 12.00 | 83.99 | 94.74 | |

As can be seen from Table 2 the pharmaceutical preparations of Examples 1 to 3 show within the first two hours in an acidic environment only very limited release of the pharmaceutically active component. Example 2 and 3 according to the present invention result in a more than 90% (substantially complete) release of the pharmaceutically active components within 8 hours or less.
In contrast thereto in the comparative formulation the pharmaceutically active component was not completely released even after 12 hours.

The invention claimed is:
1. A pharmaceutical or nutraceutical preparation comprising
 a) a core comprising a pharmaceutically or nutraceutically active substance; and
 b) an inner controlling layer surrounding the core comprising
  i) at least one (meth)acrylate copolymer bearing a cationic group or a group that can be converted to a cationic group; and
  ii) at least one copolymer bearing anionic groups or anionic groups being partially or fully neutralized by base; and
 c) an outer controlling layer consisting essentially of at least one polymer or copolymer bearing anionic groups or anionic groups being partially or fully neutralized by base,
 wherein the at least one copolymer of component ii) in the inner controlling layer comprises:
 41 to 60% by weight, based on the weight of the copolymer, of at least one structural unit derived from methyl methacrylate or ethyl acrylate; and
 40 to 59% by weight, based on the weight of the copolymer, of at least one structural unit derived from acrylic or methacrylic acid, and at least one product of at least partial neutralization thereof,
 wherein the pharmaceutically or nutraceutically active substance is released from the pharmaceutical or nutraceutical preparation in an amount of more than 90% after a first exposure to acidic conditions for 2 hours and then a subsequent exposure to neutral or alkaline conditions for 6 hours.
2. The preparation of claim 1, wherein the inner controlling layer comprises
 50 to 92% by weight of component i); and
 8 to 50% by weight of component ii),
 whereby the weight percentage is based on the total weight of polymers in the inner controlling layer.
3. The preparation of claim 2, wherein the inner controlling layer comprises
 55 to 80% by weight of component i); and
 20 to 45% by weight of component ii),
 whereby the weight percentage is based on the total weight of polymers in the inner controlling layer.
4. The preparation of claim 1, wherein component i) in the inner controlling layer comprises at least one (meth)acrylate copolymer comprising
 80 to 98% by weight, based on the weight of (meth)acrylate copolymers, of at least one structural unit derived from at least one $C_1$ to $C_4$ alkyl ester of (meth)acrylic acid; and

2 to 20% by weight, based on the weight of (meth)acrylate copolymers, of at least one structural unit derived from at least one (meth)acrylate monomer with a quaternary ammonium group in an alkyl radical of said (meth) acrylate monomer.

5. The preparation according to claim 4, wherein the at least one (meth)acrylate copolymer of component i) comprises:
   93 to 98% by weight, based on the weight of the (meth) acrylate copolymer, of at least one structural unit derived from at least one $C_1$ to $C_4$ alkyl ester of (meth)acrylic acid; and
   2 to 7% by weight, based on the weight of the (meth) acrylate copolymer, of at least one structural unit derived from at least one (meth)acrylate monomer with a quaternary ammonium group in an alkyl radical of said (meth)acrylate monomer.

6. The preparation according to claim 4, wherein the at least one (meth)acrylate copolymer of component i) comprises:
   85 to less than 93% by weight, based on the weight of the (meth)acrylate copolymer, of at least one structural unit derived from at least one $C_1$ to $C_4$ alkyl ester of (meth) acrylic acid; and
   more than 7 to 15% by weight, based on the weight of the (meth)acrylate copolymer, of at least one structural unit derived from at least one (meth)acrylate monomer with a quaternary ammonium group an alkyl radical of said (meth)acrylate monomer.

7. The preparation according to claim 4, wherein the at least one copolymer of component i) comprises a mixture of
   60 to 99% by weight, based on the total weight of the mixture, of at least one (meth)acrylate copolymer comprising 93 to 98% by weight, based on the weight of the (meth)acrylate copolymer, of at least one structural unit derived from at least one $C_1$ to $C_4$ alkyl ester of (meth) acrylic acid, and 2 to 7% by weight, based on the weight of the (meth)acrylate copolymer, of at least one structural unit derived from at least one (meth)acrylate monomer with a quaternary ammonium group an alkyl radical of said (meth)acrylate monomer; and
   1 to 40% by weight, based on the total weight of the mixture, of at least one (meth)acrylate copolymer comprising 85 to less than 93% by weight, based on the weight of the (meth)acrylate copolymer, of at least one structural unit derived from at least one $C_1$ to $C_4$ alkyl ester of (meth)acrylic acid, and more than 7% to 15% by weight, based on the weight of the (meth)acrylate copolymer, of at least one structural unit derived from at least one (meth)acrylate monomer with a quaternary ammonium group an alkyl radical of said (meth)acrylate monomer.

8. The preparation according to claim 4, wherein the at least one structural unit derived from at least one (meth) acrylate monomer with a quaternary ammonium group in an alkyl radical of said (meth)acrylate monomer is derived from triethylammoniumethyl (meth)acrylate chloride.

9. The preparation of claim 4, wherein the at least one polymer or copolymer bearing anionic groups or anionic groups being partially or fully neutralized by base in layer b) and layer c) are independently selected from at least one of the group consisting of a carboxyl functional (meth)acrylic polymer or copolymer, a carboxyl functional polysaccharide, and a product of at least partial neutralization thereof.

10. The preparation of claim 1, wherein the at least one polymer or copolymer bearing anionic groups or anionic groups being partially or fully neutralized by base in layer b) and layer c) is independently selected from at least one of the group consisting of a carboxyl functional (meth)acrylic polymer or copolymer, and a product of at least partial neutralization thereof.

11. The preparation of claim 10, wherein the carboxyl functional (meth)acrylic copolymer is selected from (meth) acrylate copolymers comprising 5 to 85% by weight of at least one structural unit comprising a carboxyl group, and 95 to 15% by weight of at least one structural unit derived from at least one alkyl ester of (meth)acrylic acid, the weight percentages being based on the weight of the carboxyl functional (meth)acrylic copolymer.

12. The preparation according to claim 11, wherein the at least one structural unit comprising a carboxyl group is derived from acrylic acid or (meth)acrylic acid.

13. The preparation according to claim 1, wherein the at least one copolymer of the outer controlling layer further consists essentially of
   60 to 95% by weight, based on the weight of the at least one copolymer in the outer controlling layer, of at least one structural unit derived from methyl (meth)acrylate or ethyl acrylate; and
   5 to 40% by weight, based on the weight of the at least one copolymer in the outer controlling layer, of at least one structural unit derived from acrylic or (meth)acrylic acid, and at least one product of at least partial neutralization thereof.

14. The preparation according to claim 1, wherein the at least one copolymer of the outer controlling layer further consists essentially of
   85 to 95% by weight, based on the weight of the at least one copolymer of the outer controlling layer, of at least one structural unit derived from methyl (meth)acrylate or ethyl acrylate; and
   5 to 15% by weight, based on the weight of the at least one copolymer of the outer controlling layer, of at least one structural unit derived from acrylic or (meth)acrylic acid, and at least one product of at least partial neutralization thereof.

15. A tablet comprising the pharmaceutical or nutraceutical preparation according to claim 1.

16. A gelatin or HPMC capsule comprising the pharmaceutical or nutraceutical preparation according to claim 1.

17. A method of increasing the release rate of a pharmaceutically or nutraceutically active substance in an aqueous or physiological fluid in a pharmaceutical or nutraceutical composition, comprising adding at least one polymer or copolymer bearing anionic groups or anionic groups being partially or fully neutralized by base to an inner controlling layer of a pharmaceutical or nutraceutical preparation comprising
   a) a core containing a pharmaceutically or nutraceutically active substance; and
   b) an inner controlling layer surrounding the core comprising: (i) at least one (meth)acrylate copolymer bearing a cationic group or a group that can be converted to a cationic group, and (ii) at least one copolymer bearing anionic groups or anionic groups being partially or fully neutralized by base; and
   c) an outer controlling layer consisting essentially of at least one polymer or copolymer bearing anionic groups or anionic groups being partially or fully neutralized by base, wherein the at least one copolymer of component (ii) in the inner controlling layer comprises 41 to 60% by weight, based on the weight of the copolymer, of at least one structural unit derived from methyl methacrylate or ethyl acrylate; and 40 to 59% by weight, based on the weight of the copolymer, of at least one structural unit derived from acrylic acid or methacrylic acid, and at least one product of at least partial neutralization thereof, wherein the pharmaceutically or nutraceutically active substance is released from the pharmaceutical or nutraceutical preparation in an amount of more than 90% after a first exposure to acidic conditions for 2 hours then a subsequent exposure to neutral or alkaline conditions for 6 hours.

18. The method of claim 17, wherein in the inner controlling layer (b) comprises:
  (i) 50 to 92% by weight of the at least one (meth)acrylate copolymer bearing a cationic group or a group that can be converted to a cationic group; and
  (ii) 8 to 50% by weight of the at least one copolymer bearing anionic groups or anionic groups being partially or fully neutralized by base,
  whereby the weight percentage is based on the total weight of polymers in the inner controlling layer.

19. The method of claim 17, wherein in the inner controlling layer (b) comprises:
  (i) 55 to 80% by weight of the at least one (meth)acrylate copolymer bearing a cationic group or a group that can be converted to a cationic group; and
  (ii) 20 to 45% by weight of the at least one copolymer bearing anionic groups or anionic groups being partially or fully neutralized by base,
  whereby the weight percentage is based on the total weight of polymers in the inner controlling layer.

20. The preparation of claim 1, wherein component (ii) of the inner controlling layer comprises 41 to 60% by weight, based on the weight of the copolymer, of ethyl acrylate; and 40 to 59% by weight, based on the weight of the copolymer, of methacrylic acid.

21. The pharmaceutical or nutraceutical preparation of claim 1, wherein the outer controlling layer consists of (i) the at least one polymer or copolymer bearing anionic groups or anionic groups being partially or fully neutralized by base and (ii) a nonionic emulsifier.

22. The method of claim 17, wherein the outer controlling layer consists of (i) the at least one polymer or copolymer bearing anionic groups or anionic groups being partially or fully neutralized by base and (ii) a nonionic emulsifier.

* * * * *